(12) United States Patent
Horseman et al.

(10) Patent No.: US 12,220,252 B2
(45) Date of Patent: Feb. 11, 2025

(54) METHOD AND SYSTEM FOR USING INTERNET OF WORKPLACE THINGS (IOWT) TO ENHANCE WORKFORCE PRODUCTIVITY

(71) Applicant: SAUDI ARABIAN OIL COMPANY, Dhahran (SA)

(72) Inventors: Samantha J. Horseman, Dhahran (SA); Wassim Basrawi, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 367 days.

(21) Appl. No.: 17/815,910

(22) Filed: Jul. 28, 2022

(65) Prior Publication Data

US 2024/0032863 A1 Feb. 1, 2024

(51) Int. Cl.
| | |
|---|---|
| G08B 23/00 | (2006.01) |
| A61B 5/00 | (2006.01) |
| G10L 15/22 | (2006.01) |
| H04L 51/02 | (2022.01) |

(52) U.S. Cl.
CPC .............. *A61B 5/486* (2013.01); *G10L 15/22* (2013.01); *H04L 51/02* (2013.01)

(58) Field of Classification Search
CPC ................ A61B 5/486; A61B 2503/24; A61B 5/02055; G10L 15/22; H04L 51/02
See application file for complete search history.

(56) References Cited

U.S. PATENT DOCUMENTS

| | | | |
|---|---|---|---|
| 9,454,751 B1* | 9/2016 | Dickerson .......... | G06Q 10/1091 |
| 10,193,981 B2 | 1/2019 | Cook | |
| 10,426,358 B2 | 10/2019 | Barnett, Jr. et al. | |
| 2015/0298654 A1 | 10/2015 | Joao et al. | |

(Continued)

FOREIGN PATENT DOCUMENTS

DE 102011109908 B4 1/2017

OTHER PUBLICATIONS

Kirichek et al.; "Model Networks for Internet of Things and SDN", IEEE; 2016 18th International Conference on Advanced Communication Technology (ICACT); Jan. 31, 2016; pp. 1-4 (4 pages).

(Continued)

*Primary Examiner* — Toan N Pham
(74) *Attorney, Agent, or Firm* — Osha Bergman Watanabe & Burton LLP

(57) ABSTRACT

A method for using an Internet of Workplace Things (IoWT) to enhance productivity in a workplace includes obtaining real-time data for a plurality of core modules via an environmental sensory system which is operatively connected to one or more core computational linguistics technologies of a workplace interface in the workplace. The method further includes analyzing the real-time data and monitoring trends by comparing the real-time data with predetermined baselines for each of the plurality of core modules. The method further includes generating a corrective real-time bio-feedback loop by providing backend solutions and commands for each core module with alerts and flags. The method further includes reporting a decision-making matrix for the backend solutions and commands. The decision-making matrix is based on the plurality of core modules as aligned with a plurality of human-machine interfaces.

19 Claims, 13 Drawing Sheets

(56) References Cited

U.S. PATENT DOCUMENTS

| | | |
|---|---|---|
| 2017/0345420 A1 | 11/2017 | Barnett, Jr. |
| 2018/0093092 A1 | 4/2018 | Howard |
| 2018/0188704 A1* | 7/2018 | Cella .................. G05B 19/0423 |
| 2019/0227626 A1 | 7/2019 | Mohammadrezazadeh et al. |
| 2021/0192419 A1* | 6/2021 | Von Troll ................. G07C 9/28 |
| 2021/0264374 A1* | 8/2021 | Vo ........................ G06V 40/161 |

OTHER PUBLICATIONS

R. Kirichek and A. Koucheryavy; "Internet of Things Laboratory Test Bed", Wireless Communications, Networking and Applications; Lecture Notes in Electrical Engineering; vol. 348; Oct. 29, 2015; pp. 485-494 (10 pages).

Li et al.; "Learning IoT in Edge: Deep Learning for the Internet of Things with Edge Computing", IEEE Network; vol. 32; Issue 1; Jan. 26, 2018; pp. 96-101 (6 pages).

X. Che and S. Maag; "A Passive Testing approach for protocols in Internet of Things", 2013 IEEE International Conference on Green Computing and Communications and IEEE Internet of Things and IEEE Cyber, Physical and Social Computing; Aug. 2013; pp. 678-684 (7 pages).

* cited by examiner

METHOD AND SYSTEM FOR USING INTERNET OF WORKPLACE THINGS (IOWT) TO ENHANCE WORKFORCE PRODUCTIVITY

BACKGROUND

The nature of work has become more challenging in recent couple of years due to infectious disease threats such as COVID-19. Most organizations are deploying digital transformation programs especially during COVID-19 pandemic workforce and leadership challenges. Now, many workers from globally interdependent communities participate in a variety of remote teams, via synchronous and asynchronous digital communication. However, traditional teamwork problems such as conflict and coordination can escalate quickly in virtual teams. Since virtual teams are now new 'normal' for many workers even post-pandemic, it is important to recognize the challenges and adopt best practices. The Internet of Things (IoT) is the explosive growth of devices connected and controlled by the Internet and has seen major significant trend in recent years. However, such technology remains fragmented and often redundant. With wide range of real-world applications in industries of all kinds—including manufacturing, transportation, energy, agriculture, retail, and government—it is desirable to implement IoT solutions to provide smarter and safer ways of connecting people, task and performance for efficient and effective work productivity, creativity, and innovation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method for using an Internet of Workplace Things (IoWT) to enhance productivity in a workplace includes: obtaining real-time data for a plurality of core modules via an environmental sensory system which is operatively connected to one or more core computational linguistics technologies of a workplace interface in the workplace. The method further includes analyzing the real-time data and monitoring trends by comparing the real-time data with predetermined baselines for each of the plurality of core modules. The method further includes generating a corrective real-time bio-feedback loop by providing backend solutions and commands for each core module with alerts and flags. The method further includes reporting a decision-making matrix for the backend solutions and commands. The decision-making matrix is based on the plurality of core modules as aligned with a plurality of human-machine interfaces.

In another aspect, embodiments disclosed herein generally relate to a workplace system that includes a smart mirror with an in-built camera and a microphone; a visual data collection camera; a computing system to support a plurality of Artificial Intelligence (AI) enabled applications and devices with combined edge-computing and high-speed wireless internet access; a speech recognition module comprising one or more core computational linguistics technologies; and an acquisition device coupled to an environmental sensory system in a workplace. The environmental sensory system is configured to capture input from the workplace. The workplace system further includes a plurality of human-machine interfaces coupled to the acquisition device and the speech recognition module; and a simulator including the computing system. The simulator is operatively coupled to the human-machine interface and includes functionality for obtaining real-time data for a plurality of core modules via an environmental sensory system which is operatively connected to one or more core computational linguistics technologies of a workplace interface in the workplace. The simulator further includes functionality for analyzing the real-time data and monitoring trends by comparing the real-time data with predetermined baselines for each of the plurality of core modules. The simulator further includes functionality for generating a corrective real-time bio-feedback loop by providing backend solutions and commands for each core module with alerts and flags. The simulator further includes functionality for reporting a decision-making matrix for the backend solutions and commands. The decision-making matrix is based on the plurality of core modules as aligned with a plurality of human-machine interfaces.

In another aspect, embodiments disclosed herein generally relate to a non-transitory computer readable medium storing instruction. The instructions are executable by a computer processor and include functionality for: obtaining real-time data for a plurality of core modules via an environmental sensory system which is operatively connected to one or more core computational linguistics technologies of a workplace interface in the workplace. The instructions further include analyzing the real-time data and monitoring trends by comparing the real-time data with predetermined baselines for each of the plurality of core modules. The instructions further include generating a corrective real-time bio-feedback loop by providing backend solutions and commands for each core module with alerts and flags. The instructions further include reporting a decision-making matrix for the backend solutions and commands. The decision-making matrix is based on the plurality of core modules as aligned with a plurality of human-machine interfaces.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1A:
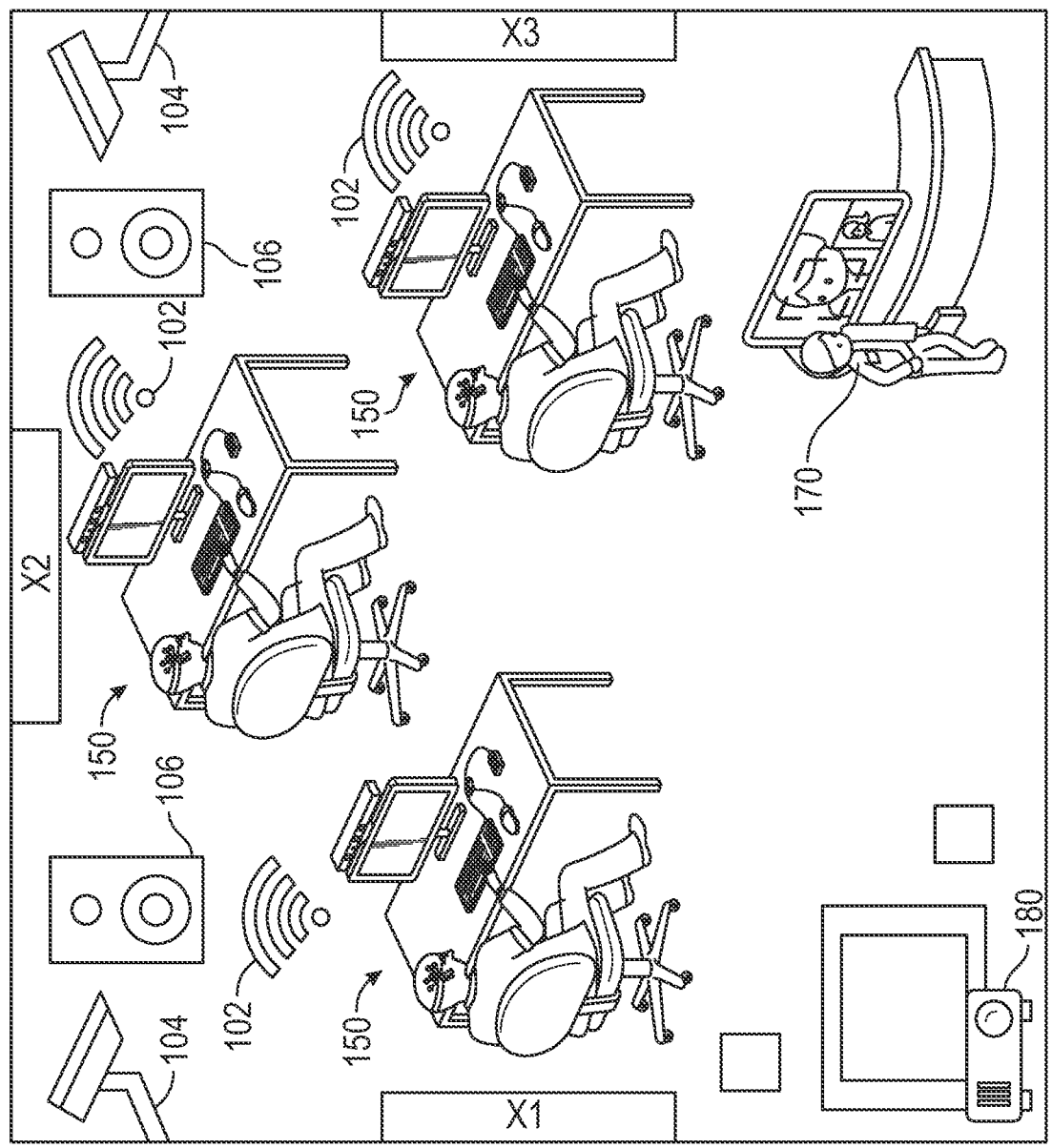
FIGS. 1A and 1B show exemplary system diagrams in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (for example, first, second, third) may be used as an adjective for an element (that is, any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-6B, any component described with regard to a figure, in various embodiments of the invention, may be equivalent to one or more like-named components described with regard to any other figure. For brevity, descriptions of these components will not be repeated with regard to each figure. Thus, each and every embodiment of the components of each figure is incorporated by reference and assumed to be optionally present within every other figure having one or more like-named components. Additionally, in accordance with various embodiments of the invention, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a horizontal beam" includes reference to one or more of such beams.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope of the invention should not be considered limited to the specific arrangement of steps shown in the flowcharts.

Although multiply dependent claims are not introduced, it would be apparent to one of ordinary skill that the subject matter of the dependent claims of one or more embodiments may be combined with other dependent claims.

In general, embodiments disclosed herein are directed to a system and a method for Internet of Workplace Things (IoWT) and equipment towards enhancing workforce productivity, engagement and empowerment via an environmental sensory auditory, human-machine interface and voice recognition system through various modules. In particular, embodiments disclosed herein may implement a plurality of human-machine engagement and empowerment, predictive methods, and a management alert system. This method utilizes identification methods of vocal prompts and commands via an environmental sensory system connected to two core computational linguistics technologies. The core computational linguistics technologies include voice recognition and natural language processing (NLP) chatbots with layered digital processing (cameras). The outputs from such auditory and visual human sensory systems may produce anticipated alerts and supervisory instructions from employees at a workplace to chatbots and the decision-making cloud via 5G network and edge computing.

Other embodiments may provide additional data-stream human-machine interfaces such as brain computer interface (BrCI) and a body machine interface (BoMI) to contribute to human intelligence across the modules. In one or more embodiments, this system includes six core modules with four key functions each clustered into "specific voice triggered & human-machine interface commands." The environmental sensory system learns from auditory prompts and cues then produces a corrective real-time biofeedback loop. The system may also provide backend solutions/commands for each of the core modules and functions.

Embodiments disclosed herein may provide a highly responsive predictive machine learning system related to the nature of work and 'new normal' of connecting to a workplace remotely that is systematically linked to entire human interfaces, for example, both body-machine and brain-machine interfaces, and adapts to end-user input. Workplace personnel are enabled to make more informed decisions and provide support across the multi-systems and data (e.g., work output, decision making, performance, employee engagement & empowerment, health & wellbeing, transformational leadership, and strategic key performance indicators).

FIG. 1A shows a schematic diagram of a workplace (100) in accordance with one or more embodiments. Specifically, the workplace (100) of an organization may include a high-speed wireless internet (102), a plurality of security cameras (104), a plurality of wireless speakers (106), a plurality of employee interfaces (150), a touchscreen reception (170), and a smart meeting room (180). A detailed description of the employee interface (150) is discussed in detail in FIG. 1B.

In some embodiments, the workplace (100) may be an office space equipped with IoT devices, and thus connected to the internet, is often referred to as a "smart office". The workplace (100) represents an intelligent ecosystem that relies on a number of connected devices that, in general, monitor, control, and manage various operations and working conditions. The workplace (100) may use technology to help employees work more productively and efficiently, whether employees are working in the office or are working remotely and connecting into the office infrastructure. The same way smart consumer technology learns and adapts to changing needs, the workplace (100) may use analytics and connected technology to ensure the organization is equipped for the specific needs of employees at any given time.

The workplace (100) may combine a variety of different tools and technologies to support more productive and automated work. The workplace (100) may provide real-time prescriptive/predictive and deep learning both with cloud, edge computing and 5G to assist leaders and workers in various work environments to connect and perform at their best whether onsite or remotely. The workplace (100) may help team and company leaders build working environments that work for the present and the future of work. By implementing technologies to adapt offices to people's evolving preferences, organizations may provide more productive environments for employees to do their best work, and build spaces that integrate with the latest tools and technologies so spaces can keep growing smarter with time.

The workplace (100) tools may include video conferencing software and hardware tools, meeting room and desk reservation software, and office analytics tools to provide insight into how different office spaces are being used. For example, the smart meeting room (108) may use intelligent technology to integrate software and hardware tools within the physical meeting room space to create a highly productive meeting experience, no matter where attendees are located. For example, the smart meeting room (108) may implement a version of or something similar to Internet of Things (IoT), also referred to herein as Internet of Workplace Things (IoWT) to connect all of the components of the workspace, integrate the workspace for remote sharing, etc. The smart meeting room (108) may help meeting participants benefit from more productive meetings over time, and help company and IT leaders glean more information about how tools and spaces are being used, so spaces can become more productive over time.

The workplace (100) may also help IT and facilities leaders understand how spaces are being used so they can better plan for office moves, renovations, and changes to better suit the needs of their workforce such that time and funds aren't being wasted where it isn't impactful. Finally, the workplace (100) may help co-located employees connect quickly and productively with other employees, customers, or clients around the world. Smart technologies and optimized space make the workplace (100) fast and easy to schedule, launch, and hold hybrid meetings, no matter where in the office meetings are held or where employees are working. A detailed description of the workplace (100) with respect to the embodiments disclosed herein is discussed in detail in FIGS. 2-4.

The workplace (100) is prepared to adapt to the evolving communication styles and may provide the data, resources, and tools to make the future of work as productive as possible. A detailed description of an implementation of the workplace (100) based on the embodiments disclosed herein (an office of the future (520)) is discussed in detail in FIG. 5B.

Figure 1B:
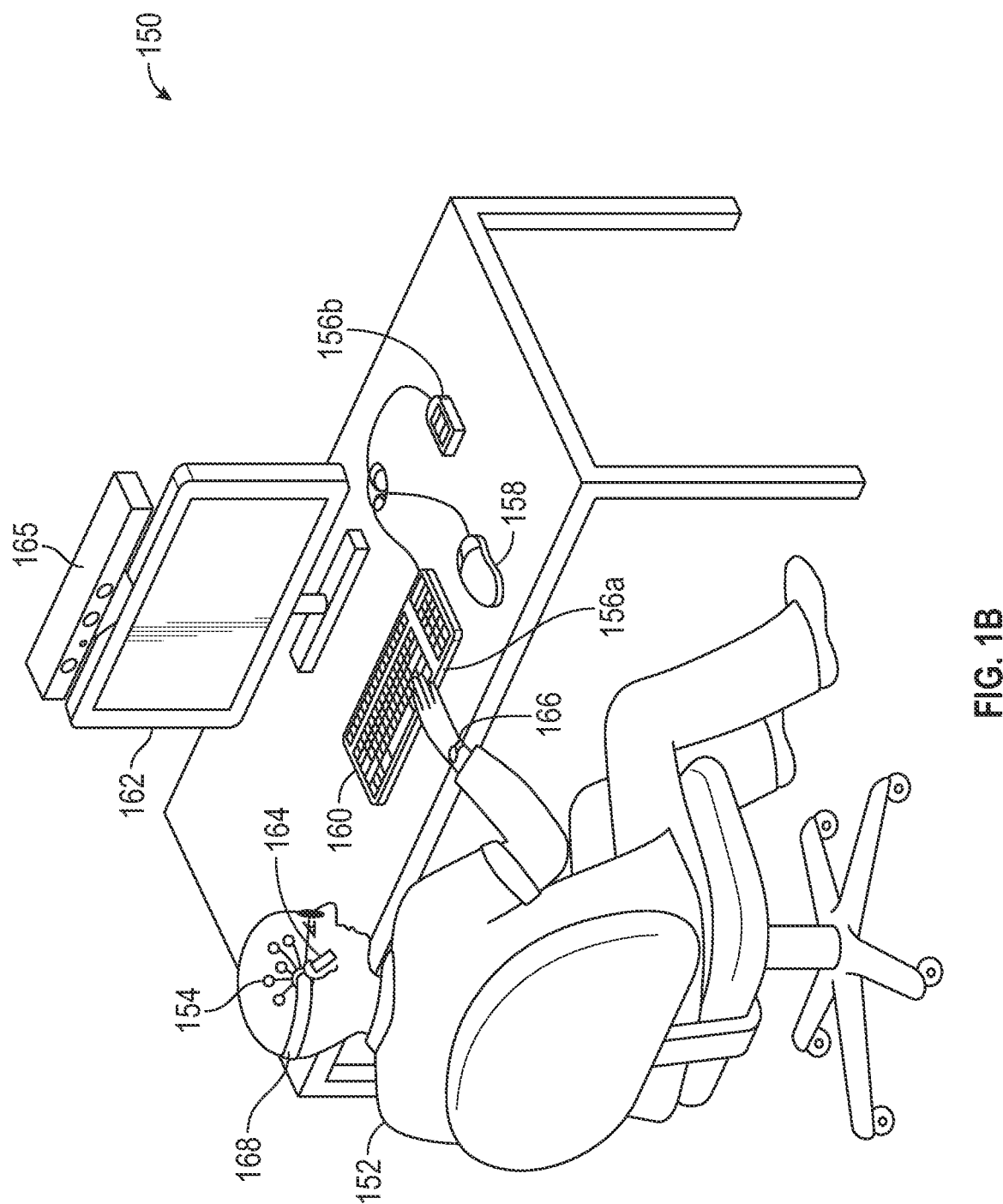

FIG. 1B shows a schematic of the employee interface (150) in accordance with one or more embodiments. Specifically, the employee interface (150) may include an employee (152), various sensors (154), various input devices, for example, a mouse (158), a keyboard (160), a microphone (164), and a camera (165). The employee interface (150) may further include a fingerprint scanner for secure login (156A and 156B), a personal computer (162), a wearable device such as a smartwatch/smart band (166), and a smart glass (168). There may be a plurality of such employee interfaces (150) in a workplace (100). A detailed description of an implementation of the employee interface (150) based on the embodiments disclosed herein is discussed in detail in FIG. 5C.

Figure 2A:
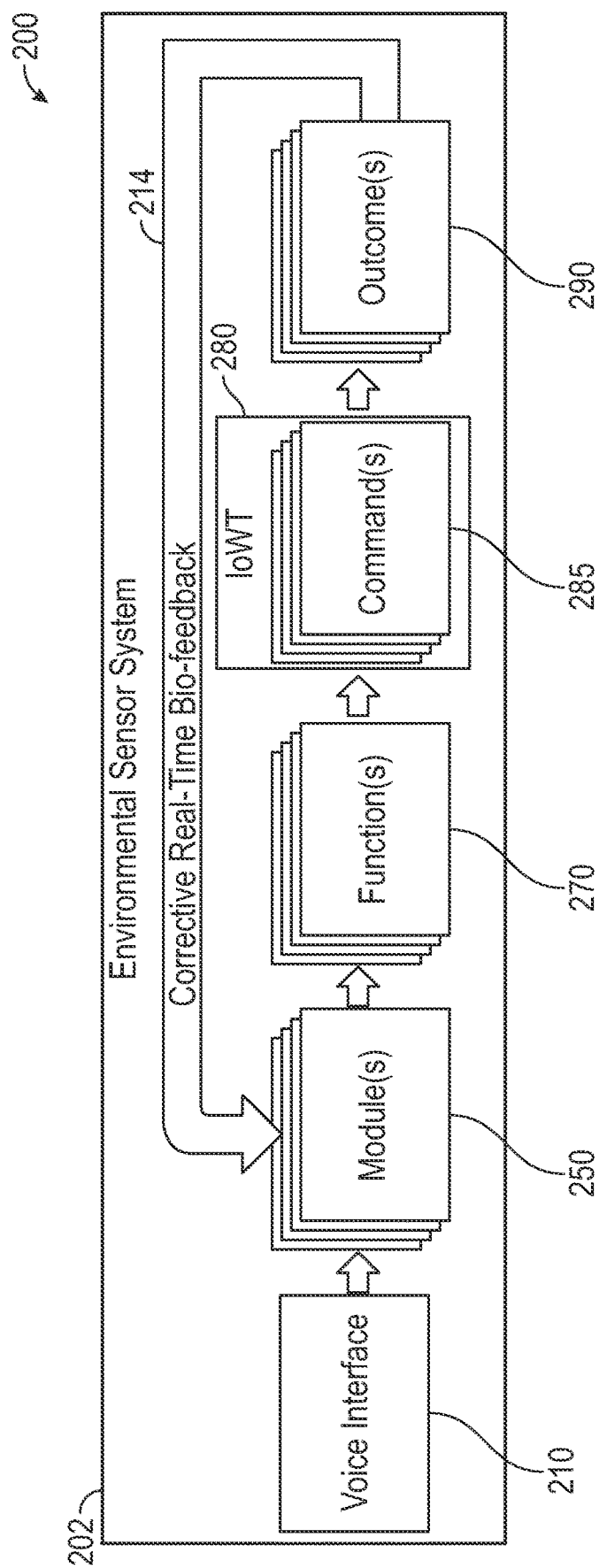
FIGS. 2A-2C show exemplary process block diagrams in accordance with one or more embodiments.

FIG. 2A shows an exemplary process block diagram in accordance with one or more embodiments. In particular, FIG. 2A shows a process block diagram (200) which includes an environmental sensory system (202), a voice interface (210), a plurality of modules (250), a plurality of functions (270) depending on the nature of the module (250), an IoWT (280) including a plurality of commands (285) for performing the function (270), and a plurality of outcomes (290) depending on the commands (285) of the IoWT (280). A corrective real-time bio-feedback loop (214) is generated based on the outcome (290) which is fed back to the plurality of modules (250). Each of these blocks are discussed in detail below.

In one or more embodiments, the IoWT may be both hardware and software that connect workplace devices and personnel using employee interfaces, for example. The IoWT may include dedicated hardware, HMIs, voice activation, and edge- or cloud-computing capabilities, and a smart display such as a smart mirror which is able to capture user/employee information by observation, gestures, touch, etc. IoWT (280) is discussed in further detail below. IoWT may further include a protocol or set of protocols that provide a map for connecting devices in the workplace using the hardware described above.

Figure 2B:
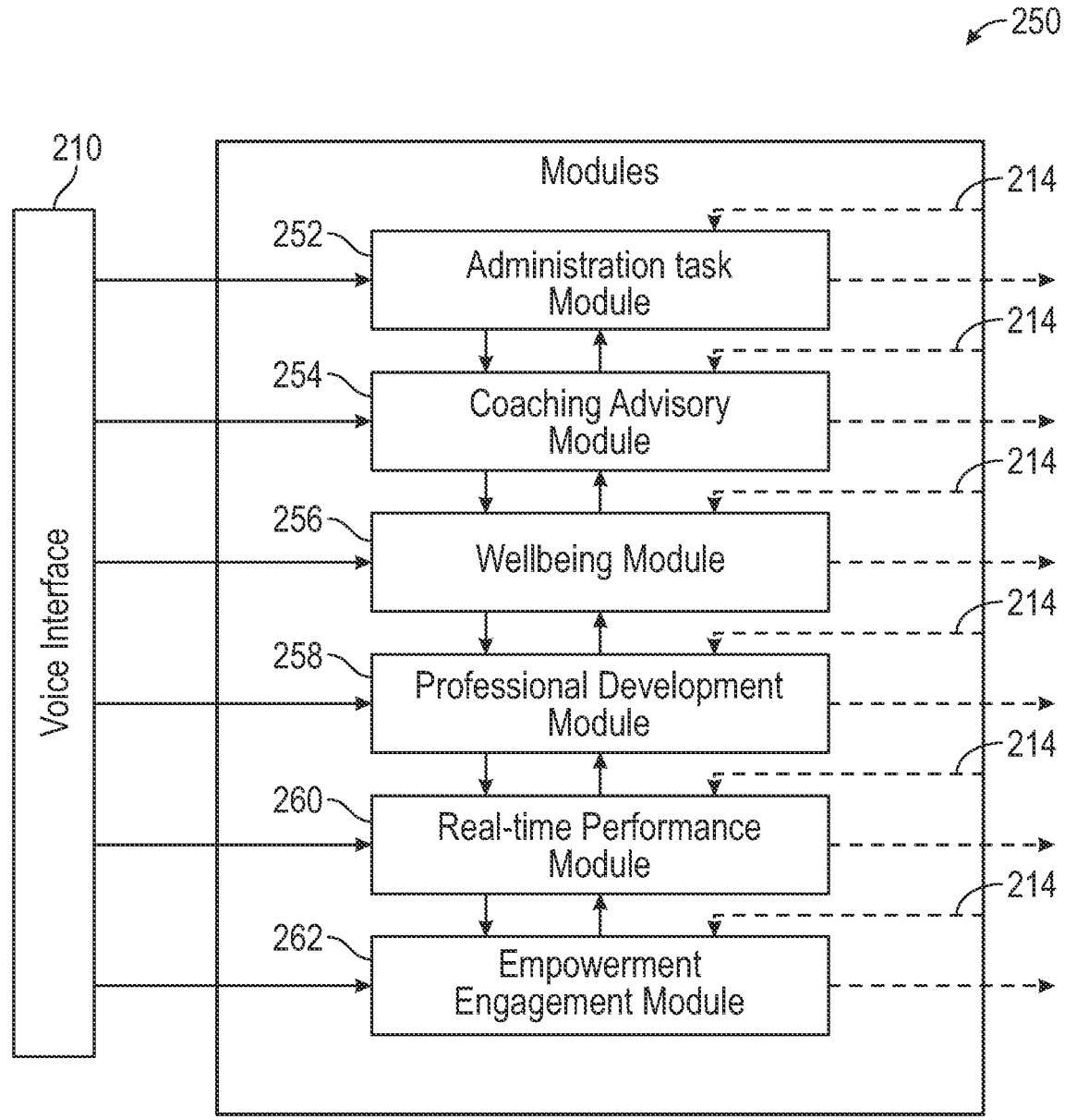

FIG. 2B shows different modules (250) used in the process of FIG. 2A (200) in accordance with one or more embodiments. In particular, in one or more embodiments, the process involves a plurality of modules (250) including, for example, an administration task module (252), a coaching advisory module (254), a wellbeing module (256), a professional development module (258), a real-time performance module (260), and an empowerment engagement module (262). Each module receives the corrective real-time bio-feedback (214) individually as shown in FIG. 2B. All of the modules (250) receive input from the voice interface (210) and send immediate output to the next connected module and to the functions (270) shown in FIG. 2A. The voice interface (210) may include various environmental sensory auditory input, a human-machine interface, and a voice recognition system (natural language processing and digital processing). The voice interface (210) may employ voice recognition algorithms that may be machine learned large speech datasets. In some embodiments, the voice interface (210) may include a speech recognition module (400) described with regard to FIG. 4A and the accompanying description.

Turning to FIGS. 2A and 2B, in some embodiments, the administration task module (252) relates to logistic and administrative transactions of the workplace (100) shown in FIG. 1A. The administration task module (252) may have various functions related to administering, for example, vacation booking, stationary/supplies requirement, calendar/task list, and creative work for all employees of different departments of the workplace (100). Different commands (285) may be given to the IoWT (280) by the employee (152) using the PC/mobile application (162) to perform desired operations from the functions (270). For example, the employee (152) may give commands like, "book vacation," "order stationary," or "book an appointment for meeting regarding project X." Based on the voice commands (285), the IoWT (280) may pull up different options and may couple with (c/w (286)) a dashboard (metrics) (288), shown in FIG. 2C, to display the pulled up options as the outcomes (290) for administration tasks, for example, "general personal issues," "appointment/calendar," or "job logistics and planning." In some embodiments, based on the administration tasks performed, the corrective real-time bio-feedback (214) is fed back to the administration task module (252) which is further shared with the next module, for example, the coach advisory module (254) as shown in FIG. 2B.

In some embodiments, the coach advisory module (254) relates to knowledge transaction of the workplace (100). The coach advisory module (254) may have various functions related to, for example, real-time coach, just-in time (JIT) coach, inner potential, and talent development for all employees of different departments of the workplace (100). Different commands (285) may be given to the IoWT (280)

by the employee (152) using the PC/mobile application (162) to perform desired operations from the functions (270). For example, the employee (152) may give commands like, "how do I develop and deploy project management?," "what is the best way to present my case?," or "how to learn and enhance analytical skills?." Based on the commands (285), the IoWT (280) may pull up different options and may couple with (c/w (286)) the dashboard (metrics) (288), shown in FIG. 2C, to display the pulled up options as the outcomes (290) for coach tasks, for example, "verification of ability," "JIT support," "personalized/customized coaching," or "job logistics and planning." In some embodiments, based on the coach tasks performed, the corrective real-time bio-feedback (214) is fed back to the coach advisory module (254) which is further shared with the next module, for example, the wellbeing module (256) as shown in FIG. 2B.

In some embodiments, the wellbeing module (256) relates to keep well and balanced transaction of the workplace (100). The wellbeing module (256) may have various functions related to, for example, physical wellbeing plan, mental wellbeing plan, social wellbeing plan, and spiritual wellbeing plan for all employees of different departments of the workplace (100). Again, various commands (285) may be given to the IoWT (280) by the employee (152) for the wellbeing module (256). For example, the employee (152) may give commands like, "call my wellbeing coach," "I am stressed, HELP!," or "take me to my mindfulness session." Based on the commands (285), the IoWT (280) may pull up different options and may couple with (c/w (286)) the dashboard (metrics) (288), shown in FIG. 2C, to display the pulled up options as the outcomes (290) for wellbeing tasks, for example, "advice work/life balance," "energized," "high performance," or "connected/content." In some embodiments, based on the wellbeing task performed, the corrective real-time bio-feedback (214) is fed back to the wellbeing module (256) which is further shared with the next module, for example, the development module (258) as shown in FIG. 2B.

In some embodiments, the development module (258) relates to JIT training/transaction of the workplace (100). The JIT training may require a lot of support and effort from a business. The most important aspect is the cultivation of a learning culture in the organization. In order to adopt a just in time training model successfully, learning has to be a fundamental part of the business. In this regard, training is not treated as a separate process, but rather an integral aspect of the business itself. The development module (258) may have various functions related to, for example, IT module, leadership module, job specific, and competencies for all employees of different departments of the workplace (100). Different commands (285) may be given to the IoWT (280) by the employee (152) using the PC/mobile application (162) to perform desired operation from the functions (270). For example, the employee (152) or may give commands like, "enroll me into a management course," "I need to develop factor analysis algorithm," or "I need to find a better phrase for 'adjunction'." Based on the commands (285), the IoWT (280) may pull up different options and may couple with (c/w (286)) the dashboard (metrics) (288), shown in FIG. 2C, to display the pulled up options as the outcomes (290) for development tasks, for example, "learning prescription," "customized," "on the job training," or "specialized learning platform." In some embodiments, based on the development tasks performed, the corrective real-time bio-feedback (214) is fed back to the development module (258) which is further shared with the next module, for example, the performance module (260) as shown in FIG. 2B.

In some embodiments, the performance module (260) relates to continuous feedback of the workplace (100). The performance module (260) may have various functions related to, for example, appreciation, monthly rating, rewards/penalty, and continuous feedback for all employees of different departments of the workplace (100). Commands (285) may be given to the IoWT (280) by the employee (152) such as "what was my overall performance score today," "book coaching session for 360°," or "how did I perform in task Y?" Based on the commands (285), the IoWT (280) may pull up different options and may couple with (c/w (286)) the dashboard (metrics) (288), shown in FIG. 2C, to display the pulled up options as the outcomes (290) for performance tasks, for example, "performance prescription," "awareness/skills gap," "knowledge gain factor," or "timeline-retrospective performance." In some embodiments, based on the performance tasks performed, the corrective real-time bio-feedback (214) is fed back to the performance module (260) which is further shared with the next module, for example, the empowerment engagement module (262) as shown in FIG. 2B.

Figure 2C:
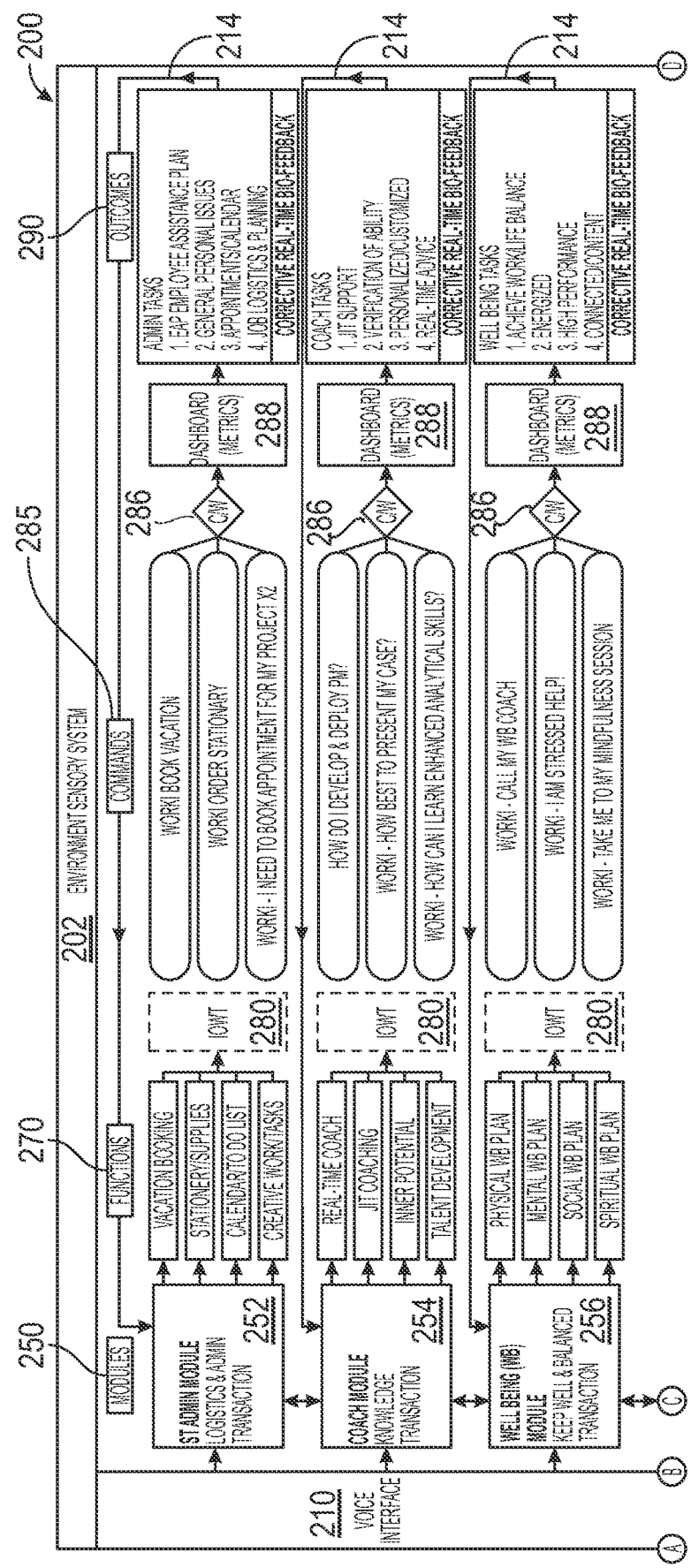
Figure 2C:
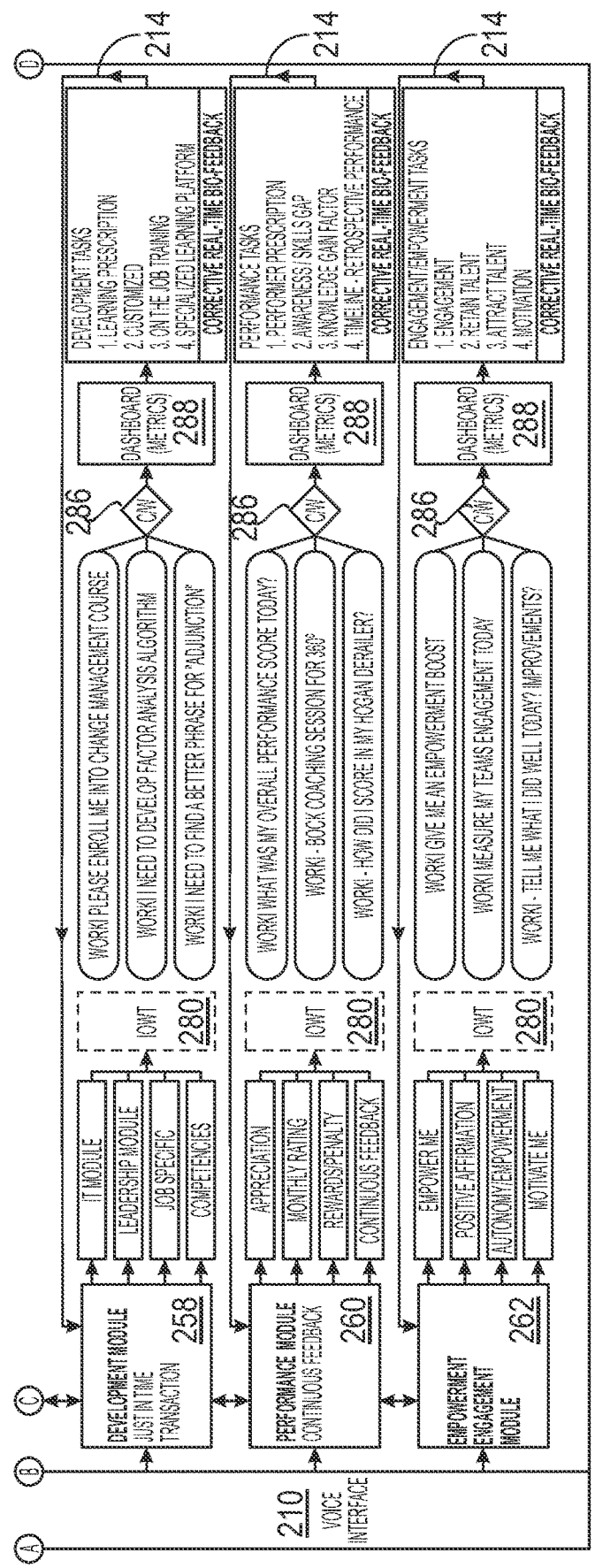

In some embodiments, the engagement empowerment module (262) relates to empowerment of the workplace (100). The engagement empowerment module (262) may have various functions related to, for example, empower me, positive affirmation, autonomy/empowerment, and motivate me for all employees of different departments of the workplace (100). Commands (285) that may be given to the IoWT (280) by the employee (152) may include, for example, "give me an empowerment boost," "measure my teams' engagement today," or "tell me what I do well today? improvements?" Based on the commands (285), the IoWT (280) may pull up different options and may couple with (c/w (286)) the dashboard (metrics) (288), shown in FIG. 2C, to display the pulled up options as the outcomes (290) for engagement empowerment tasks, for example, "engagement," "retain talent," "attract talent," or "motivation." In some embodiments, based on the engagement empowerment tasks performed, the corrective real-time bio-feedback (214) is fed back to the performance module (260) in real-time as shown in FIG. 2B. FIG. 2C depicts synergistic relationships of each module and the biofeedback loop in the process block diagram (200) that determines the human machine interface (HMI) performance.

In one or more embodiments, the IoWT (280) may incorporate four key elements with respect to the employee (152), for example, self-awareness (human machine interface (HMI)), detection system (real-time data streaming module), adaption system (personnel, tasks, equipment, and environment), and situational awareness (decision making matrix). The four key elements are described in detail below in context of the workplace (100):

1). Self-awareness (human machine interface)—The employee (152) performs with the BrCI and BoMI systems. Meanwhile, real-time data streaming from the body computer interface and brain computer interface (hardware) feeds into the detection system (software). For example, Arduino™ shield (computing system) has Bluetooth™ capacity and data streams wirelessly for latent data streams via 5G. In addition, the real-time data is captured via an edge computing onsite. The HMIs form a map connecting the worker across the systems—i.e., the worker is connected to the work task, which in turn is connected to the workspace, in turn connected to the work environment, and then connected to the organization. Each level of the map is one layer of abstraction above the inner layer, forming, in one or more embodiments, a 5-layer system map connected by the HMIs.

2). Detection system (real time data streaming module)—Data analyses and trends are monitored and tracked into three modules. The data is compared with baselines. For example, white flag (normal operations), yellow flag (warning of a potential threat or vulnerability), red flag (crisis—high alert—immediate action required). The required real-time actions are explained in the next component of adaptation as the real-time corrective bio-feedback loop (214).

3). Adaptation system (personnel, tasks, equipment, and site environment)—White alerts are tracked for baseline monitoring of various work-tasks. Yellow alerts are adapted for by the employee (152) and then signaled forward to alert edge devices. Red alerts are automatically simultaneously sent to a manager for further investigation.

4). Situational awareness (supervisory—decision making matrix)—This module is the reporting phase to insure efficient and effective work operations. This decision matrix is based on the system modules as aligned with human assets, task management, environmental controls, and organizational integrity aligned with operational excellence at the workplace (100).

Figure 3:
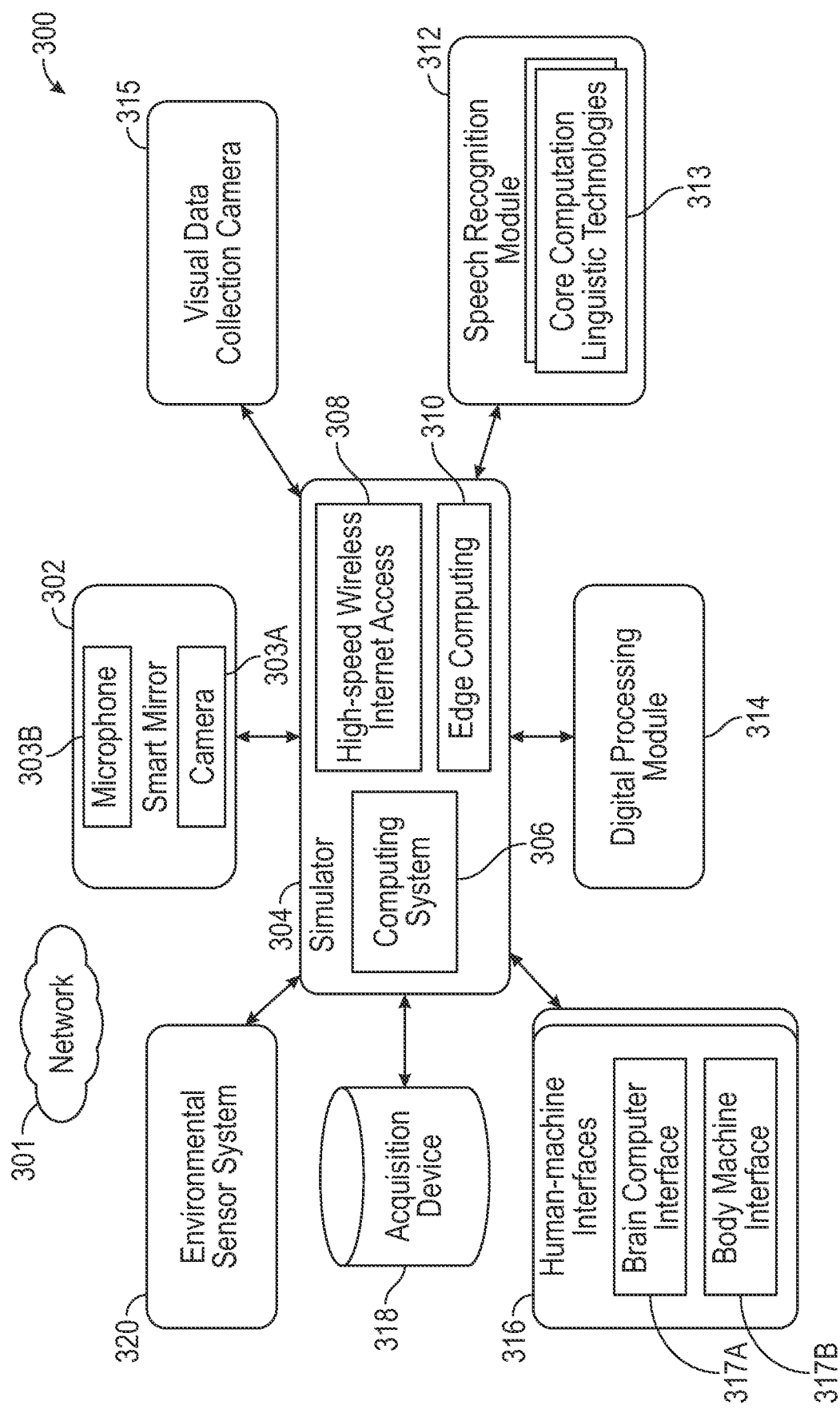
FIG. 3 shows an exemplary system hardware diagram in accordance with one or more embodiments.

Turning to FIG. 3, FIG. 3 shows an exemplary system hardware diagram in accordance with one or more embodiments. More specifically, FIG. 3 illustrates various major hardware components required for setting up the IoWT (280) that is used for enhancing workplace productivity, engagement, and empowerment via an environmental sensory auditory, human-machine interface, and voice recognition system through various modules as shown in FIGS. 1 and 2. In particular, the system for IoWT (300) includes a network (301), a smart mirror (302), a computing system (306), a speech recognition module (312), a digital processing module (314), a visual data collection camera (315), a plurality of human-machine interfaces (316), an acquisition device (318), and an environmental sensory system (320). The simulator (304) and computing system (306) may be further operatively connected to a high-speed wireless internet access (308) and an edge computing (310). The speech recognition module (312) may further include one or more core computational linguistics technologies (313). Each of these components are discussed in detail below.

In one or more embodiments, the smart mirror (302) is used in the IoWT (280) in alignment with the human-machine interfaces (316) to hyper-connect the employee with the task, equipment, workspace, environment, and organization at large with the corrective real-time bio-feedback loop. The smart mirror (302) may be a motion-activated and supported by mobile/computer operating systems (for example, Android™, iOS™, Windows, Linux and OS X) which may be used for receiving inputs from the employee and displaying output after processing of the commands from the employee. The smart mirror (302) may be controlled with voice commands, gestures, and touch and may support connection to other devices/equipment through different options, for example, Wi-Fi, Bluetooth™ ethernet cable or universal serial bus ports (USB). In some embodiments, the visual data collection camera (315) is operatively connected to the smart mirror (302) or the smart mirror (302) may have an in-built camera (303A) and a microphone (303B) to obtain commands and gestures of the employee for different operations of the IoWT (280). The smart mirror (302) may have various applications already installed and may have options to install different applications per work requirement. The smart mirror (302) may be operatively connected to other hardware or software components of the IoWT (280) through a network (301) that is similar to the network (620) described with regard to FIG. 6B and the accompanying description.

In some embodiments, the visual data collection camera (315) may be a smart camera with powerful onboard processors and image sensors into an all-in-one vision system which is managed by the network (302). The visual data collection camera (315) may have digital input/output which may further include opto-isolated digital inputs, opto-isolated digital outputs, a RS232 serial port, and Gigabit Ethernet ports. The visual data collection camera (315) may also include built-in digital I/O and industrial communication options for dynamic, real-time communication and integration with industrial automation devices including programmable logic controllers (PLCs), the human machine interfaces (316), the environmental sensory system (320), robotics, and industrial machinery.

In some embodiments, the IoWT (280) shown in FIG. 2A may be provided with a simulator (304). For example, the simulator (304) may include hardware and/or software with functionality for analyzing data and/or performing one or more IoWT simulations. For example, the simulator (304) may store logs and data regarding obtained commands from the employee for performing simulations in the acquisition device (318). The simulator (304) may further analyze the data, the commands, and/or other types of data to generate and/or update the one or more in-built models. The simulator (304) may include hardware or software with functionality for generating one or more trained models regarding implementing commands (285) shown in FIG. 2A. For example, different types of models may be trained, such as machine learning, artificial intelligence, convolutional neural networks, deep neural networks, support vector machines, decision trees, inductive learning models, deductive learning models, and supervised learning models, and are capable of approximating solutions of complex non-linear problems. The simulator (304) may couple to the computing system (306), a high-speed wireless internet access (308), and an edge computing (310) for faster and smooth processing of data.

In one or more embodiments, the high-speed wireless internet access (308), sometimes referred to as a "hot spot" if it is available to the public, is a local area network (LAN) run by radio waves rather than wires. The high-speed wireless internet access (308) is broadcast from a central hub, which is a hard-wired device that actually brings in the Internet connection. The hub, located at the main computer system or server, broadcasts Internet connectivity to clients, which includes basically anyone within receiving range who is equipped with a wireless LAN card and a password to the network (301), if the connection is secured. The edge computing (310) is a distributed computing framework that brings enterprise applications closer to data sources such as IoT devices or local edge servers. This proximity to data at its source can deliver strong business benefits, including faster insights, improved response times and better bandwidth availability.

In some embodiments, the simulator (304) may include functionality for applying artificial intelligence, machine learning, and deep learning methodologies to precisely determine various outcomes for the commands received from the employee. To do so, a large amount of interpreted data may be used to train a model. To obtain this amount of data, the simulator (304) may augment acquired data for various scenarios and situations via the environmental sensory system (320) and the core computational linguistics technologies (313), for example, voice recognition and natural language processing (NLP) chatbots with layered digital processing by the digital processing module (314). The outputs from such auditory and visual human sensory systems may produce anticipated alerts and supervisory instructions from employees to chatbots and the decision-making cloud via the network (301) and edge computing (310). In some embodiments, the simulator (304) may use data augmentation to generate a dataset that combines original acquired data with augmented data based on the environmental sensory system (320) and the core computational linguistics technologies (313). This supplemented dataset may provide sufficient training data to train a model accordingly.

In some embodiments, the computing system (306) may support various artificial intelligence enabled applications and devices with the combined high-speed wireless internet access (308) and edge-computing (310) that runs in as little as 5 watts. For example, NVIDIA® Jetson Nano™ is a small and power efficient computer for embedded applications and artificial intelligence that delivers the power of modern artificial intelligence in the real-world settings and may be implemented as the computing system (306) in the IoWT (280). In addition, the computing system (306) may have capability of running multiple neural networks in parallel for applications like image classification, object detection, segmentation, and speech processing. In some embodiments, the computing system (306) for the system for IoWT (300) is the same as or similar to that of computer system (600) described below in FIGS. 6A and 6B and the accompanying description.

In some embodiments, the speech recognition module (312) may provide the ability of a machine or program to identify words and phrases in spoken language and convert them to a machine-readable format. For example, with ubiquitous technologies such as Alexa and Siri in addition to leveraging artificial intelligence (deep learning/neural networks) via machine learning tools may now apply transcribed datasets that may create more effective and efficient speech recognition models across a given population based on a variety of voice characteristics.

Figure 4A:
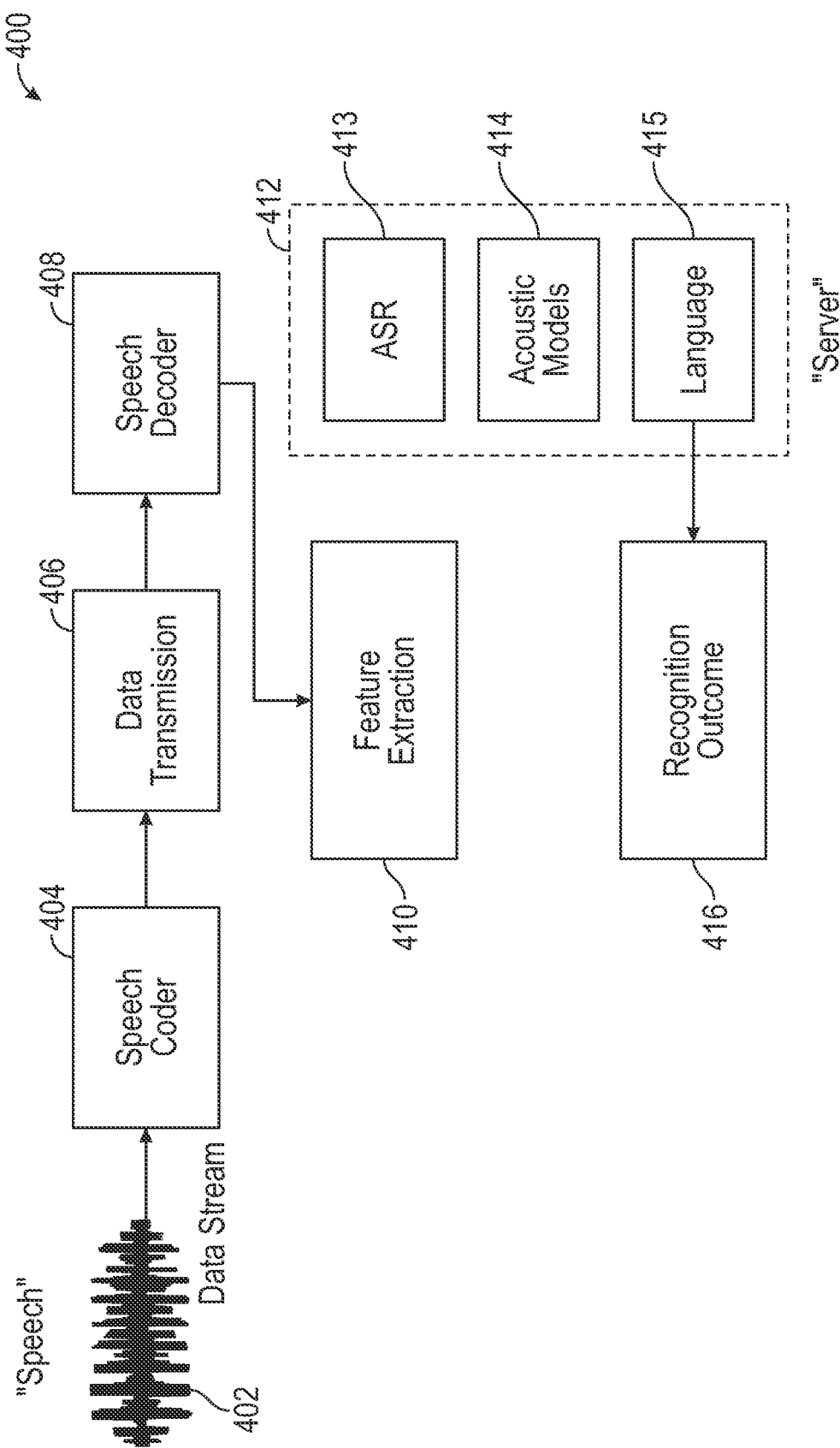
FIGS. 4A and 4B show exemplary block diagrams in accordance with one or more embodiments.

In one or more embodiments, the speech recognition module (312) may use the one or more core computational linguistics technologies (313) to process and interpret spoken words by the employee and convert them into text. FIG. 4A illustrates various major hardware components required for setting up a system (400) for the speech recognition module (312) in accordance with one or more embodiments. In particular, the system (400) includes a speech coder (404), data transmission (406), a speech decoder (408), a feature extraction (410), a server (412) and a recognition outcome (416). The server (412) further includes an automatic speech recognition (ASR) (413), a plurality of acoustic models (414), and a language (415).

In particular, after the speech (402) is obtained through the microphone (303B), shown in FIG. 3, the data stream is fed through the speech coder (404) for analyzing the audio in real-time. Once analyzed, the audio is broken into parts and passed through the data transmission (406), the speech decoder (408), and the feature extraction (410) for digitizing the audio into computer-readable format. The ASR (413) and the acoustic models (414) are used for implementing software algorithms of the core computation linguistic technologies (313) shown in FIG. 3 to match the computer-readable format to the most suitable text representation of the language (415) in the server (412) and display to the recognition outcome (416). The software algorithms of the core computation linguistic technologies (313) that process and organize audio into text are trained on different speech patterns, speaking styles, languages, dialects, accents, and phrasings. The software algorithms of the core computation linguistic technologies (313) also separate spoken audio from background noise that often accompanies the audio signal.

Figure 4B:
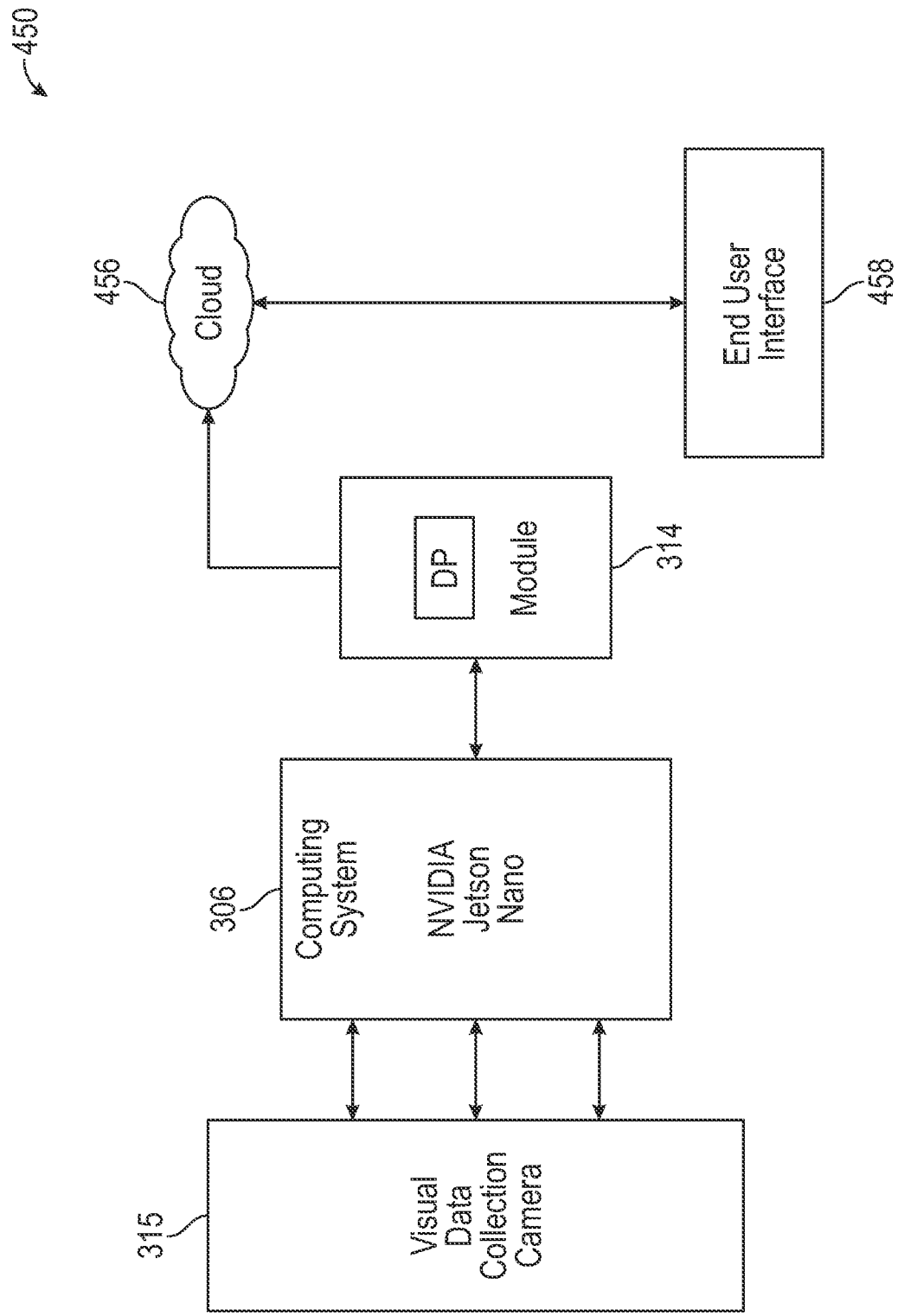

Turning to FIG. 3, the digital processing module (314) is an integrated power amplifier accessory of the system (300) for the IoWT, with numerous capabilities, designed to reduce or eliminate the need for any additional signal processing gear. FIG. 4B illustrates various major hardware components required for setting up a system (450) for implementing the digital processing module (314) in accordance with one or more embodiments. In particular, data stream received from the virtual data collection camera (315) and/or camera (303A) (not shown here) are fed to the digital processing module (314) through the computing system (306) in real-time and turn it into the digital format of 1's and 0's. The data stream may be real-world signals like voice, audio, video, temperature, pressure, or position. From here, the digital processing module (314) takes over by capturing the digitized information and processing the data stream. The digital processing module (314) then feeds the digitized information back for use in the real world via cloud (456) which may be accessed by an end user interface (458), for example, the employee PC or the employee mobile application. The digital processing module (314) may also be used as controllers for signals acquisition and processing systems as well as for control of the other devices connected through the cloud (456).

Continuing with FIG. 3, the human-machine interfaces (316) may further include a brain computer interface (BrCI) (317A) and a body machine interface (BoMI) (317B). The BoMI (317B) may have provisions to measure, for example, the heart rate in beats per minute (bpm) are either measured through digital processing/microblushes via the smart mirror (302) or through contact with input devices within work tasks, workspace, and environment; temperature in degrees (Celsius) is measured through a surface temperature sensor; galvanic skin response, where skin resistance demonstrates stress response, is measured using finger conductance and resistance (overall coherence values); biomechanical stress and emotional state in newtons/degrees are measured using a flex sensor (measurement of wrist and hip angles); and accelerometer and gyro in speed and rotation at an axis are measured using a motion and location sensor (GPS). Similarly, the BrCI (317A) may have provisions to measure using dry electrode EEG electroencephalography. In some embodiments, as an additional data-stream the BrCI (317A) and the BoMI (317B) contribute to human intelligence across the modules shown in FIG. 2B.

In some embodiments, the environmental sensory system (320) may include sensors that includes a processor, memory, and an analog-to-digital converter for processing sensor measurements. For example, the sensors may include acoustic sensors, such as accelerometers, measurement microphones, contact microphones, and hydrophones. Likewise, the sensors may include other types of sensors, such as temperature and heart rate. The sensors may include hardware or software or both for generating different types of sensory logs of the employee that may provide data about the employee and the workplace. The environmental sensory system may include smart sensors that detect events or physical changes in the environment, for example, measuring air quality and occupancy levels.

Figure 5A:
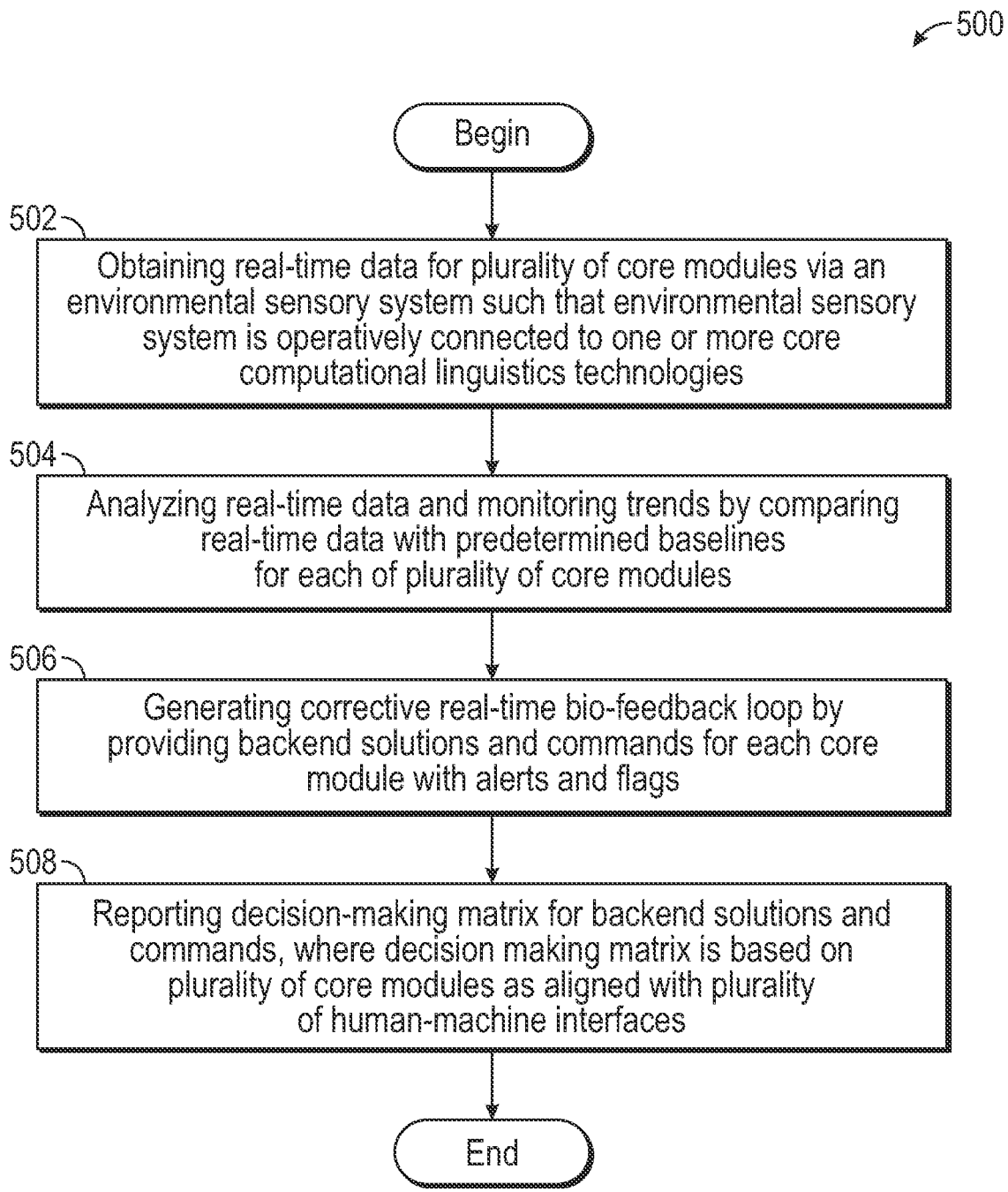
FIG. 5A shows flowchart in accordance with one or more embodiments.

FIG. 5A shows a flowchart (500) in accordance with one or more embodiments. Specifically, FIG. 5A describes a general method for internet of workplace things (IoWT), for example, computer systems and equipment for enhancing workplace productivity, engagement, and empowerment via an environmental sensory auditory, human-machine interface, and voice recognition system (NLP and digital processing) through various modules. One or more steps in FIG. 5A may be performed by one or more components (for example, modules (250), network (301), smart mirror (302), simulator (304), computer processor (306), speech recognition module (312), digital processing module (314), human machine interfaces (316), and environmental sensory system (320)) as described in FIGS. 2-3. While the various steps in FIG. 5A are presented and described sequentially, one of ordinary skill in the art will appreciate that some or all of the steps may be executed in different orders, may be combined, or omitted, and some or all of the steps may be executed in parallel. Furthermore, the steps may be performed actively or passively. The method may be repeated or expanded to support multiple components and/or multiple users within a field environment. Accordingly, the scope of the invention should not be considered limited to the specific arrangement of steps shown in the flowchart.

In step 502, real-time data is obtained for a plurality of core modules via an environmental sensory system such that the environmental sensory system is operatively connected to one or more core computational linguistics technologies in accordance with one or more embodiments. In particular, a "worker HMI" (hardware and software designed and developed at the e-factory) performs with the BrCI and BoMI system for self-awareness in which the real-time data streaming from the body computer interface and brain computer interface (hardware) is fed into the detection system (software) for six core modules as described previously in FIGS. 2A and 2B and the accompanying description. For example, the computing system (306) (e.g., Arduino shield) has Bluetooth capacity and data streams wirelessly for latent data streams via 5G (using high-speed wireless internet access (308)). In addition, the real-time data is captured via edge computing (310) onsite as described previously in FIGS. 1B and 3 and the accompanying description.

In step 504, the real-time data is analyzed and trends are monitored by comparing the real-time data with predetermined baselines for each of the plurality of core modules in accordance with one or more embodiments. For example, in real-time data streaming module, data analyses and trends are tracked into three modules for the detection system. The data is compared with baselines as described previously in FIGS. 2A and 2B and the accompanying description.

In step 506, a corrective real-time bio-feedback loop is generated by providing backend solutions and commands for each core module with alerts and flags in accordance with one or more embodiments. For example, flags generated are white flag (normal operations), yellow flag (warning of a potential threat or vulnerability), and red flag (crisis—high alert—immediate action required). The required real-time actions as a corrective biofeedback loop are generated in the form of alerts for the adaptation system as described previously in FIGS. 2A and 2B and the accompanying description. For example, white alerts are tracked for baseline monitoring of various work-tasks. Yellow alerts are adapted for by the end user and then signaled forward to alert edge devices. Red alerts are automatically simultaneously sent to manager for further investigation.

In step 508, a decision-making matrix for the backend solutions and commands is reported, the decision making matrix is based on plurality of core modules as aligned with a plurality of human-machine interfaces in accordance with one or more embodiments. For example, the situational awareness is related to the reporting phase to insure efficient and effective work operations. This decision matrix is based on the system modules as aligned with human assets, task management, environmental controls, and organizational integrity aligned with operational excellence.

Figure 5B:
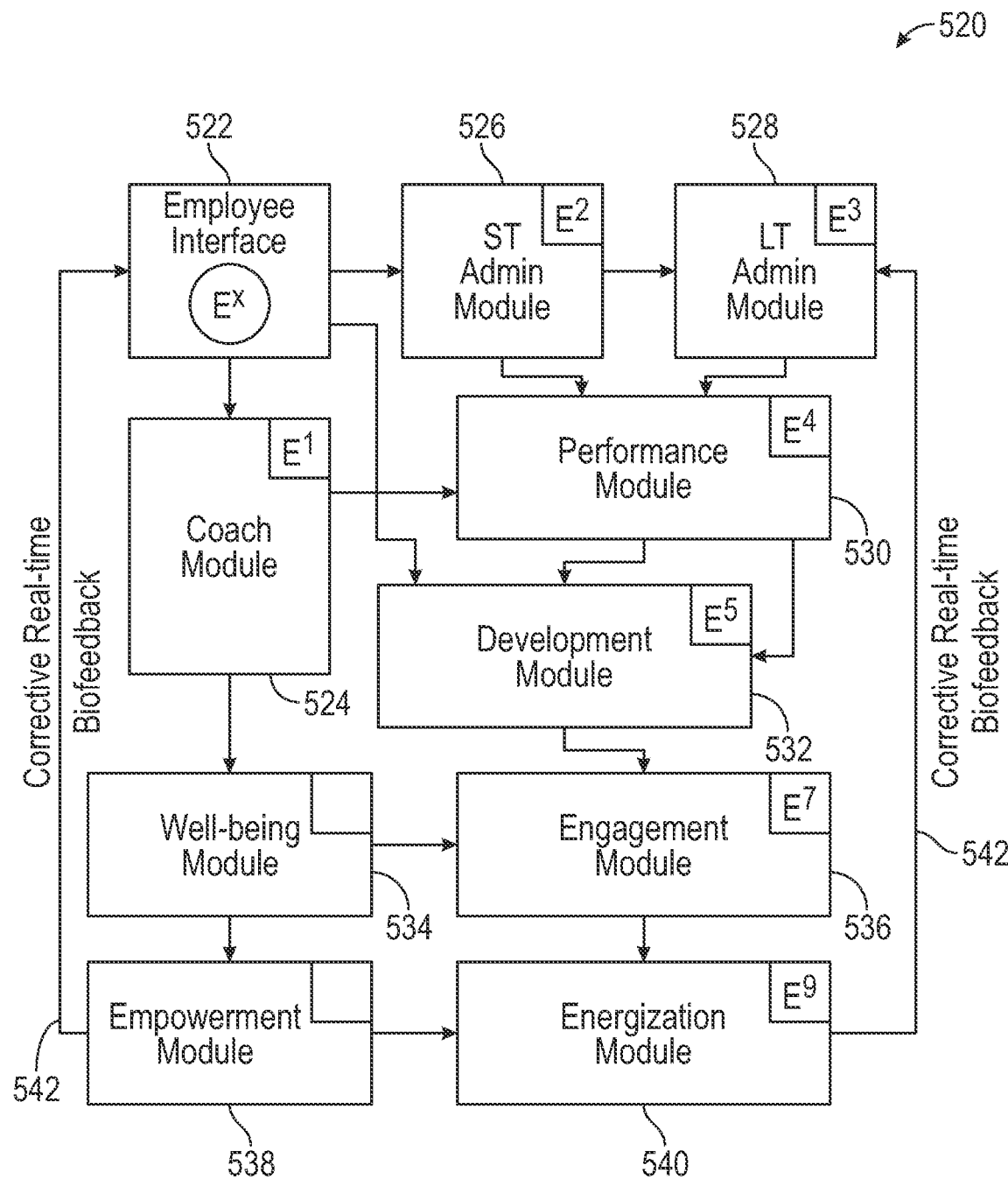
FIGS. 5B and 5C show exemplary block diagrams of FIGS. 1A and 1B, respectively, in accordance with one or more embodiments.
Figure 5C:
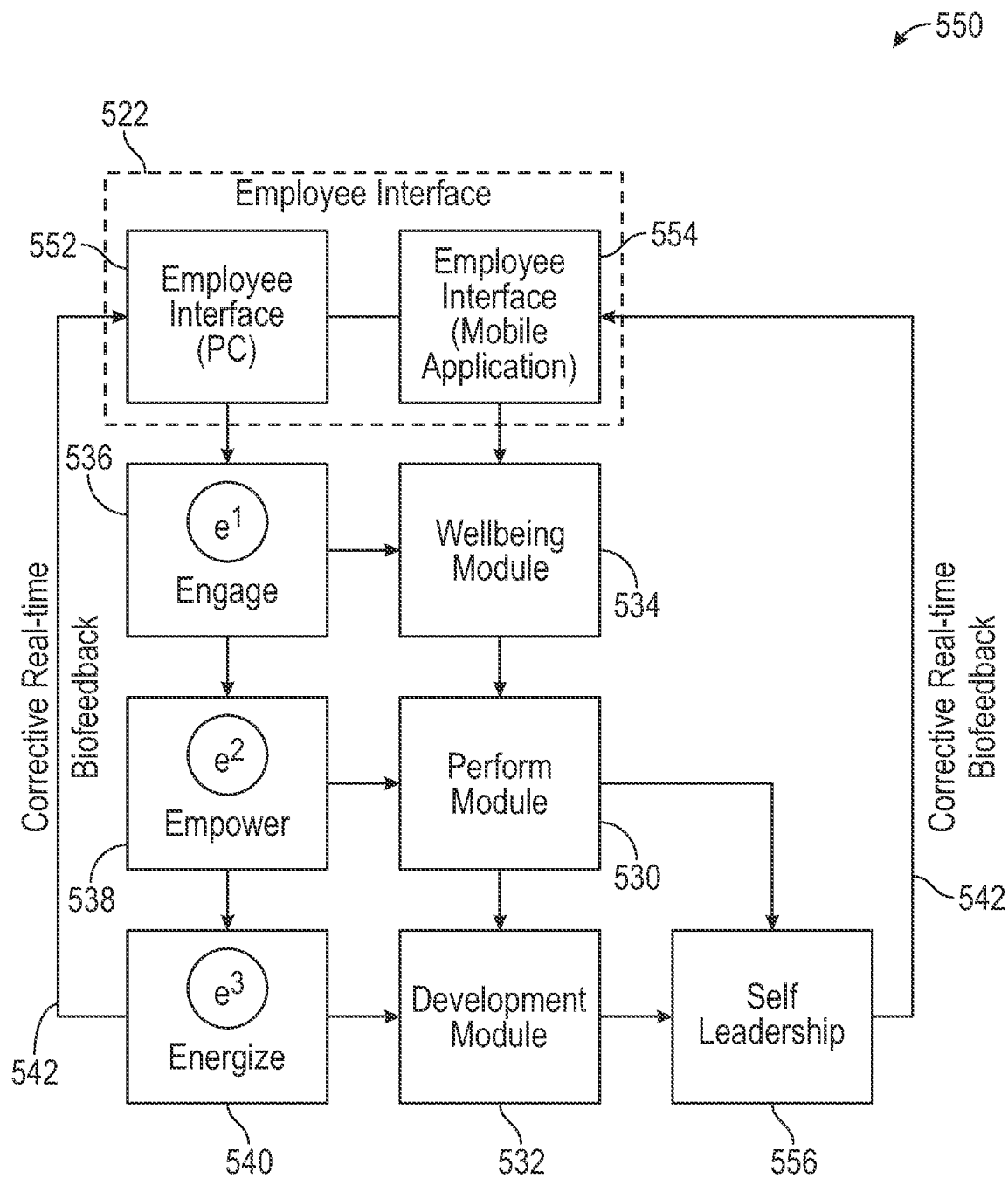

FIGS. 5B and 5C show exemplary implementations of FIGS. 1A and 1B, respectively, based on one or more embodiments. In particular, FIG. 5B shows an exemplary implementation of an office of the future (520) in accordance with one or more embodiments. The office of the future (520) may include an employee interface (522) operatively connected to a ST admin module (526) which is further connected to LT admin module (528) for logistic and admin transaction. Inputs from the employee interface (522) through environmental sensory auditory, human-machine interface, and voice recognition system (NLP and digital processing) are sent through a coach module (524) for knowledge transaction, a well-being module (534) for keeping well and balanced transaction, and an empowerment engagement module (538) for general use of an organization. The inputs from the employee interface (522) may also be sent to a development module (532) for professional development transaction, an engagement module (536) followed by an energization module (540). In some embodiments, the inputs of the employee interface (522) obtained by the admin modules (526 and 528) are fed to a performance module (530) which may further send the inputs from the employee interface (522) to the development module (532), engagement module (536), and energization module (540). A corrective real-time biofeedback (542) is generated at the end of the empowerment module (538) to the employee interface (522). In some embodiments, the corrective real-time biofeedback (542) is generated at the end of the energization module (540) to the LT admin module (528).

In some embodiments, the focus area of the office of the future (520) incorporates human-machine interfaces, digital processing, computer science, artificial intelligence, and computational linguistics. The technology is real time voice recognition and natural language processing computer system and environmental hardware/equipment that is able to predict, learn and solve day to day organizational functions, tasks, and activities. The supportive infrastructure of the office of the future (520) thus collates the data stream of various brain signal patterns on various behavioral states of the employee interface (522), for example, relaxed/clam, excitable/anxious, and task engagement/alertness, across various work tasks (modules 524-540) into the data pool of the detection system and data lake of adaption of corrective real-time biofeedback (542). The situational awareness is reinforced via the decision-making matrix. This may result in a significant impact on the workforce as it reduces the impact of stress and information overload further enhancing work performance in real time.

Turning to FIG. 5C, FIG. 5C shows an exemplary implementation of a system (550) for an employee using the employee interface (522) in accordance with one or more embodiments. The system (550) may include an employee interface (PC) (552) and an employee interface (mobile application) (554). The data stream of various brain signal patterns on various behavioral states of the employee interface (522) are collected through environmental sensory auditory, human-machine interface, and voice recognition system (NLP and digital processing) of the employee interface (PC) (552) and the employee interface (mobile application) (554), for example, relaxed/clam, excitable/anxious, and task engagement/alertness. Inputs from the employee interface (PC) (552) are sent through the engagement module (engage) (536) and inputs from the employee interface (mobile application) (554) and the engagement module (536) are sent through the well-being module (534) for keeping well and balanced transaction. In addition, output signals obtained from the engagement module (536) is further sent to the empowerment module (empower) (538), which in turn is also sent along with the output from the well-being module (534) to the performance module (530) (perform module) for continuous feedback. An output of the performance module (530) is then sent to the development module (532) for professional development transaction such as a self-leadership (556) for the employee. In some embodiments, an output from the empowerment module (538) is passed to the development module (532) via the energization module (energize) (540). The corrective real-time biofeedback (542) is generated at the end of the energization module (540) to the employee interface (PC) (552). In some embodiments, the corrective real-time biofeedback (542) is generated at the end of the self-leadership (556) to employee interface (mobile application) (554). The supportive infrastructure of the system (550) thus collates the data stream of various brain signal patterns on various behavioral states of the employee interface (522) across various work tasks (modules 530-540) into the data pool of the detection system and data lake of adaption of corrective real-time biofeedback (542).

One or more embodiments disclosed herein provides internet of workplace things via a critical systems lens in alignment with the human-machine interface that hyper-connects the worker with the task, equipment, workspace, environment and organization at large with a corrective real time bio-feedback loop. One or more embodiments may be advanced into home and car modules to use self-awareness of a user to reinforce situational awareness for the operational excellence via the decision-making matrix. In addition to advancing IoT technologies with combined edge-computing and 5G, the outcome of one or more embodiments enhances efficiency and productivity yielding enhanced company profits.

Figure 6A:
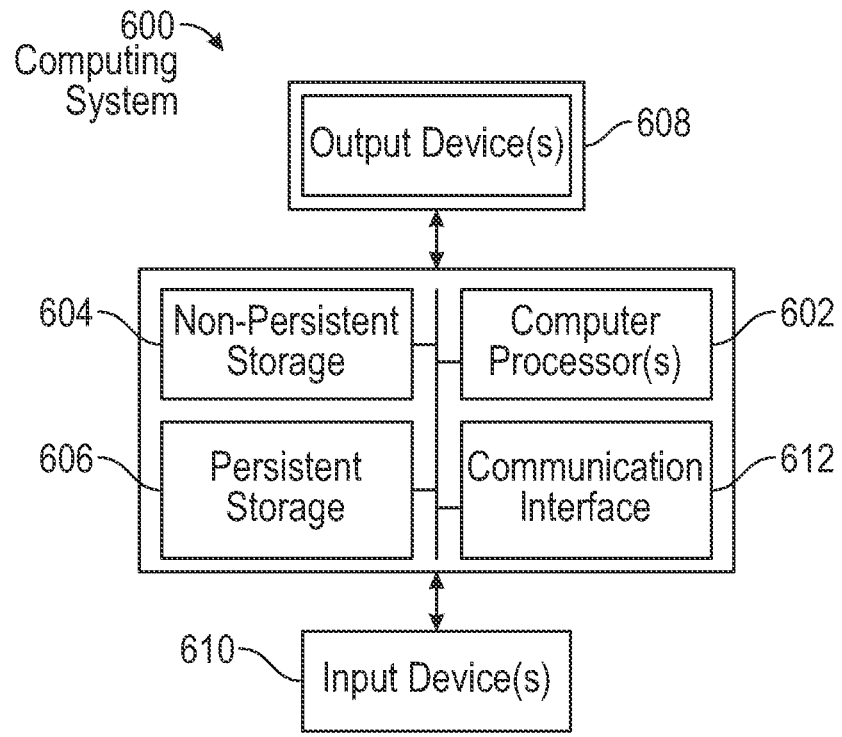
FIGS. 6A and 6B show a computing system in accordance with one or more embodiments.

Embodiments may be implemented on a computing system. Any combination of mobile, desktop, server, router, switch, embedded device, or other types of hardware may be used. For example, as shown in FIG. 6A, the computing system (600) may include one or more computer processors (602), non-persistent storage (604) (for example, volatile memory, such as random access memory (RAM), cache memory), persistent storage (606) (for example, a hard disk, an optical drive such as a compact disk (CD) drive or digital versatile disk (DVD) drive, a flash memory), a communication interface (612) (for example, Bluetooth interface, infrared interface, network interface, optical interface), and numerous other elements and functionalities.

The computer processor(s) (602) may be an integrated circuit for processing instructions. For example, the computer processor(s) may be one or more cores or micro-cores of a processor. The computing system (600) may also include one or more input devices (610), such as a touch-screen, keyboard, mouse, microphone, touchpad, or electronic pen.

The communication interface (612) may include an integrated circuit for connecting the computing system (600) to a network (not shown) (for example, a local area network (LAN), a wide area network (WAN), such as the Internet, mobile network, or any other type of network) or to another device, such as another computing device.

Further, the computing system (600) may include one or more output devices (608), such as a screen (for example, a liquid crystal display (LCD), a plasma display, touchscreen, cathode ray tube (CRT) monitor, or projector), a printer, external storage, or any other output device. One or more of the output devices may be the same or different from the input device(s). The input and output device(s) may be locally or remotely connected to the computer processor(s) (602), non-persistent storage (604), and persistent storage (606). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that when executed by a processor(s) is configured to perform one or more embodiments of the disclosure.

Figure 6B:
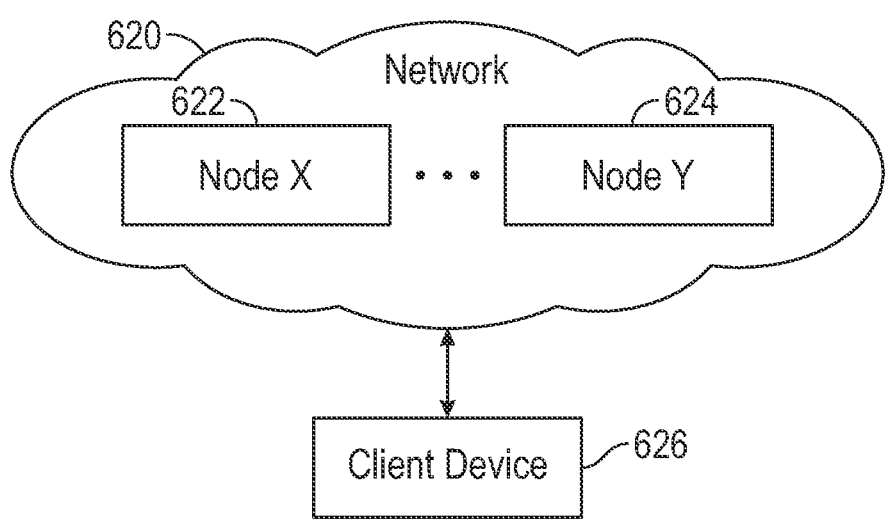

The computing system (600) in FIG. 6A may be connected to or be a part of a network. For example, as shown in FIG. 6B, the network (620) may include multiple nodes (for example, node X (622), node Y (624)). Each node may correspond to a computing system, such as the computing system shown in FIG. 6A, or a group of nodes combined may correspond to the computing system shown in FIG. 6A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (600) may be located at a remote location and connected to the other elements over a network.

Although not shown in FIG. 6B, the node may correspond to a blade in a server chassis that is connected to other nodes via a backplane. By way of another example, the node may correspond to a server in a data center. By way of another example, the node may correspond to a computer processor or micro-core of a computer processor with shared memory or resources.

The nodes (for example, node X (622), node Y (624)) in the network (620) may be configured to provide services for a client device (626). For example, the nodes may be part of a cloud computing system. The nodes may include functionality to receive requests from the client device (626) and transmit responses to the client device (626). The client device (626) may be a computing system, such as the computing system shown in FIG. 6A. Further, the client device (626) may include or perform all or a portion of one or more embodiments of the disclosure.

The computing system or group of computing systems described in FIGS. 6A and 6B may include functionality to perform a variety of operations disclosed herein. For example, the computing system(s) may perform communication between processes on the same or different systems.

A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided in subsequent paragraphs.

Based on the client-server networking model, sockets may serve as interfaces or communication channel endpoints enabling bidirectional data transfer between processes on the same device. Foremost, following the client-server networking model, a server process (for example, a process that provides data) may create a first socket object. Next, the server process binds the first socket object, thereby associating the first socket object with a unique name or address. After creating and binding the first socket object, the server process then waits and listens for incoming connection requests from one or more client processes (for example, processes that seek data). At this point, when a client process wishes to obtain data from a server process, the client process starts by creating a second socket object. The client process then proceeds to generate a connection request that includes at least the second socket object and the unique name or address associated with the first socket object. The client process then transmits the connection request to the server process. Depending on availability, the server process may accept the connection request, establishing a communication channel with the client process, or the server process, busy in handling other operations, may queue the connection request in a buffer until the server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (for example, bytes).

Shared memory refers to the allocation of virtual memory space in order to substantiate a mechanism for which data may be communicated or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

The computing system of FIG. 6A may include functionality to present raw or processed data, such as results of comparisons and other processing. For example, presenting data may be accomplished through various presenting methods. Specifically, data may be presented through a user interface provided by a computing device. The user interface may include a GUI that displays information on a display device, such as a computer monitor or a touchscreen on a handheld computer device. The GUI may include various GUI widgets that organize what data is shown as well as how data is presented to a user. Furthermore, the GUI may present data directly to the user, for example, data presented as actual data values through text, or rendered by the computing device into a visual representation of the data, such as through visualizing a data model.

For example, a GUI may first obtain a notification from a software application requesting that a particular data object be presented within the GUI. Next, the GUI may determine a data object type associated with the particular data object, for example, by obtaining data from a data attribute within the data object that identifies the data object type. Then, the GUI may determine any rules designated for displaying that data object type, for example, rules specified by a software framework for a data object class or according to any local parameters defined by the GUI for presenting that data object type. Finally, the GUI may obtain data values from the particular data object and render a visual representation of the data values within a display device according to the designated rules for that data object type.

The previous description of functions presents only a few examples of functions performed by the computing system of FIG. 6A and the nodes or client device in FIG. 6B. Other functions may be performed using one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed. Accordingly, the scope of the disclosure should be limited only by the attached claims.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112(f) for any limitations of any of the claims herein, except for those in which the claim expressly uses the words 'means for' together with an associated function.

What is claimed:

1. A method for using an Internet of Workplace Things (IoWT) to enhance productivity in a workplace, comprising:
   obtaining, using a computer processor, real-time data for a plurality of core modules via an environmental sensory system, wherein the environmental sensory system is operatively connected to one or more core computational linguistics technologies of a workplace interface in the workplace;
   analyzing, using the computer processor, the real-time data and monitoring trends by comparing the real-time data with predetermined baselines for each of the plurality of core modules;
   generating, using the computer processor, a corrective real-time bio-feedback loop by providing backend solutions and commands for each core module with alerts and flags; and
   reporting, using the computer processor, a decision-making matrix for the backend solutions and commands,
   wherein the decision-making matrix is based on the plurality of core modules as aligned with a plurality of human-machine interfaces.

2. The method of claim 1, further comprising producing the alerts and supervisory instructions based on an output of the environmental sensory system and the predetermined baselines.

3. The method of claim 1, further comprising streaming the real-time data from a body computer interface and a brain computer interface for a plurality of modules via the environmental sensory system.

4. The method of claim 1, wherein the core modules consist of an administration task module, a coaching advisory module, a wellbeing module, a professional development module, a real-time performance module, and an empowerment engagement module.

5. The method of claim 1, wherein the corrective real-time bio-feedback loop indicates the flags for real time actions of adaptation.

6. The method of claim 1, wherein the flags for the real time actions consisting of a white flag for normal operations, a yellow flag for warning of a potential threat, and a red flag for a crisis and high alert.

7. The method of claim 1, wherein the alerts consist of white alerts for tracking baseline monitoring, yellow alerts for signaling forward to alert devices, and red alerts for further investigation.

8. A workplace system, comprising:
   a smart mirror with an in-built camera and a microphone;
   a visual data collection camera;
   a computing system to support a plurality of Artificial Intelligence (AI) enabled applications and devices with combined edge-computing and high-speed wireless internet access;
   a speech recognition module comprising one or more core computational linguistics technologies;
   an acquisition device coupled to an environmental sensory system in a workplace, the environmental sensory system being configured to capture input from the workplace;
   a plurality of human-machine interfaces coupled to the acquisition device and the speech recognition module; and
   a simulator comprising the computing system, wherein the simulator is operatively coupled to the plurality of human-machine interfaces and comprises functionality for:
   obtaining real-time data for a plurality of core modules via an environmental sensory system, wherein the environmental sensory system is operatively connected to the one or more core computational linguistics technologies;
   analyzing the real-time data and monitoring trends by comparing the real-time data with predetermined baselines for each of the plurality of core modules;
   generating a corrective real-time bio-feedback loop by providing backend solutions and commands for each core module with alerts and flags; and
   reporting a decision-making matrix for the backend solutions and commands,
   wherein the decision-making matrix is based on the plurality of core modules as aligned with the plurality of human-machine interfaces.

9. The system of claim 8, wherein the plurality of human-machine interfaces further comprises a brain computer interface and a body machine interface.

10. The system of claim 9, further comprising a plurality of input devices, a plurality of output devices and a plurality of storage devices coupled with the brain computer interface and the body machine interface.

11. The system of claim 9, wherein the simulator is further configured to stream the real-time data from the body machine interface and the brain computer interface for a plurality of modules via the environmental sensory system.

12. The system of claim 8, wherein the speech recognition module further comprises the one or more core computational linguistics technologies, voice recognition, and natural language processing (NLP) chatbots.

13. The system of claim 8, wherein the simulator is further configured to produce the alerts and supervisory instructions based on an output of the environmental sensory system, the speech recognition module, and a digital processing module.

14. A non-transitory computer readable medium storing instructions executable by a computer processor, the instructions comprising functionality for:
   obtaining real-time data for a plurality of core modules via an environmental sensory system, wherein the environmental sensory system is operatively connected to one or more core computational linguistics technologies of a workplace interface in a workplace;
   analyzing the real-time data and monitoring trends by comparing the real-time data with predetermined baselines for each of the plurality of core modules;
   generating a corrective real-time bio-feedback loop by providing backend solutions and commands for each core module with alerts and flags; and
   reporting a decision-making matrix for the backend solutions and commands,
   wherein the decision-making matrix is based on the plurality of core modules as aligned with a plurality of human-machine interfaces.

15. The non-transitory computer readable medium of claim 14, wherein the instructions further comprise functionality for:
   producing the alerts and supervisory instructions based on an output of the environmental sensory system and the predetermined baselines; and
   streaming the real-time data from a body computer interface and a brain computer interface for a plurality of modules via an environmental sensory system.

16. The non-transitory computer readable medium of claim 14, wherein the core modules consist of an administration task module, a coaching advisory module, a wellbeing module, a professional development module, a real-time performance module, and an empowerment engagement module.

17. The non-transitory computer readable medium of claim 14, wherein the corrective real-time bio-feedback loop provides the flags for real time actions of adaptation.

18. The non-transitory computer readable medium of claim 14, wherein the flags for the real time actions consisting of a white flag for normal operations, a yellow flag for warning of a potential threat, and a red flag for a crisis and high alert.

19. The non-transitory computer readable medium of claim 14, wherein the alerts consist of white alerts for tracking baseline monitoring, yellow alerts for signaling forward to alert devices, and red alerts for further investigation.

* * * * *